US006204036B1

(12) United States Patent
Metzner et al.

(10) Patent No.: US 6,204,036 B1
(45) **Date of Patent: *Mar. 20, 2001**

(54) STABLE TRANSGLUTAMINASE PREPARATIONS AND PROCESSES FOR THEIR PRODUCTION

(75) Inventors: Hubert Metzner, Lahntal; Hermann Karges, Marburg, both of (DE)

(73) Assignee: Aventis Behring GmbH, Marburg (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/999,702

(22) Filed: Dec. 22, 1997

Related U.S. Application Data

(63) Continuation of application No. 08/614,934, filed on Mar. 11, 1996, now abandoned.

(30) Foreign Application Priority Data

Mar. 9, 1995 (DE) ............................................. 195 08 192

(51) Int. Cl.[7] ....................................................... C12N 9/96
(52) U.S. Cl. ......................... 435/188; 424/94.5; 435/193
(58) Field of Search .................................... 435/193, 188; 424/94.5

(56) References Cited

U.S. PATENT DOCUMENTS 4,297,344 * 10/1981 Schwinn et al. ..................... 530/381
4,327,086 * 4/1982 Fukushima et al. ................... 514/21
5,164,373 * 11/1992 Shikano et al. ........................ 514/21
5,518,742 * 5/1996 Soeda et al. ........................... 426/63

FOREIGN PATENT DOCUMENTS 20 63 070 6/1972 (DE) .
0 018 561 11/1980 (EP) .
0 037 078 10/1981 (EP) .
0 637 451 2/1995 (EP) .
53-59018 5/1978 (JP) .
92/00767 1/1992 (WO) .
93/03147 2/1993 (WO) .
93/15234 8/1993 (WO) .

OTHER PUBLICATIONS

Karges, et al., "Production and Virus Safety of Human F XIII Concentrates", 1993, pp. 66–76.
Metzner, et al., "Recombinant Factor XIII—Biochemical Properties", 1993, pp. 87–93.

* cited by examiner

*Primary Examiner*—Leon B. Lankford, Jr.
(74) *Attorney, Agent, or Firm*—Foley & Lardner

(57) ABSTRACT

The present invention relates to stable preparation forms of a transglutaminase, for example factor XIII, which, after lyophilization, are readily soluble without turbidity. The preparation froms comprise, in addition to the transglutaminase additives selected from the group consisting of D- and/or L-amino acids other than glycine and arginine, their salts, derivatives and homologs, or dimers or oligomers thereof or mixtures thereof, and sugars or sugar alcohols. The formulations may also comprise surface active agents and/or reducing agents. The invention provides processes for preparing stable protein preparations and to the use of the described stable preparation forms for producing pharmaceuticals which are suitable, for example, for treating diseases which are characterized by F XIII deficiency.

37 Claims, No Drawings

STABLE TRANSGLUTAMINASE PREPARATIONS AND PROCESSES FOR THEIR PRODUCTION

This application is a continuation of application Ser. No. 08/614,934, filed Mar. 11, 1996 abandoned.

FIELD OF THE INVENTION

The present invention relates to stable transglutaminase preparations, in particular stable preparations of factor XIII, processes for producing stable transglutaminases, and their therapeutic uses.

BACKGROUND OF THE INVENTION

Transglutaminases are $Ca^{2+}$ dependent enzymes that catalyze the formation of isopeptide bonds in proteins between the side chain γ-carboxamide group of glutamine and the side chain ε-amino group of lysine. Transglutaminases are found both extracellularly and intracellularly. Examples of transglutaminases include Factor XIII, epidermal transglutaminases, type II transglutaminases (tissue type transglutaminase, liver transglutaminases), and type I transglutaminases (keratinocyte transglutaminase).

Factor XIII (F XIII, fibrin-stabilizing factor), is a transglutaminase found as a proenzyme in plasma, platelets and monocytes/macrophages. It is important, inter alia, for ensuring efficient blood coagulation and would healing. F XIII, isolated from placenta or plasma or in the form of fresh frozen plasma, has ben employed for many years for treatment of factor XIII deficiency. It recently has become possible to prepare factor XIII using recombinant DNA technology. As used herein, rF XIII refers to recombinant factor XIII.

Commercially available purified or partially purified transglutaminase or F XIII preparations contain added stabilizers, such as human serum albumin (HSA). The use of protein stabilizers is problematic, since it decreases protein specific activity, increases the protein load when administered to patients, and may interfere with assessment of purity. It may also make the protein preparation immunogenic. These disadvantages of protein stabilizers make them particularly disadvantageous for stabilizing highly purified proteins, such as recombinant proteins. Additionally, use of protein stabilizers causes potential contamination with viral antigens when albumin, for example, is added.

The composition and activity of protein preparations used in therapy must be stable over relatively long periods of time. It is only rarely possible to achieve this stability in solution and, therefore, such products are frequently marketed in the dry state. Mild freeze-drying (lyophilization) is the method of choice for drying such products. However, even when this method is used, stable preparations fulfilling the requirements for integrity and durability are difficult to achieve.

Freeze-drying of unstabilized transglutaminase solutions leads, for example, to a marked drop in activity and to considerable turbidity. Formulations based on albumin and containing relatively high concentrations of salts have, therefore, been previously described for use with purified F XIII preparations. See, for example, DE-C-2063 070 and JP 53/59018. These formulations, however, suffer from the disadvantage described above of containing foreign protein, with all the problems attached thereto.

The freeze-drying of rF XIII in the presence of glycine or arginine and non-reducing sugars has been described. See WO 90/03147. Neither the stability, solubility, nor clarity of the reconstituted lyophilisate was described, however. The products obtained were stored at −20° C., indicating that the lyophilized material probably had inadequate stability at 4° C.

It is apparent, therefore, that a stable lyophilized formulation for transglutaminases, in particular for F XIII, is greatly to be desired. It is desirable such a formulation can be administered locally (e.g. topically) or parenterally, is stable at 2–8° C. (or higher) and does not require the addition of protein stabilizers, for example, HSA. Furthermore, the lyophilisate should be readily soluble and, following dissolution, should yield a stable, non-turbid solution.

SUMMARY OF THE INVENTION

The present invention comprises, inter alia, a stable lyophilized transglutaminase formulation, comprising at least one additive selected from the group consisting of: D- and L- amino acids and salts, derivatives, homologs, dimers, and oligomers thereof; sugars or sugar alcohols; surface-active agents; and reducing agents, with the proviso that the additive is neither glycine nor arginine, and wherein the formulation is readily soluble without any turbidity.

The instant invention further comprehends a formulation wherein the transglutaminase is selected from the group consisting of Factor XIII, and biologically active fragments, derivatives, and muteins thereof.

The instant invention further comprehends a formulation, wherein the Factor XIII is recombinant Factor XIII or is isolated from plasma, placenta, thrombocyte, or macrophages/monocytes. The instant invention also comprehends a formulation, wherein the amino acid is selected from the group consisting of His, Glu, Met, Thr, Lys, Ala, Ile, or Cys, and the salts, derivatives, homologs, dimers and oligomers thereof. The formulation additionally includes a formulation wherein the sugar or sugar alcohol is selected from the group consisting of sucrose, maltose, trehalose, lactose, sorbitol, mannitol, and the derivatives, and homologs thereof and a formulation, which further includes an amino acid selected from the group consisting of His, Glu, Ile and Ala.

The formulation of the present invention also includes a formulation wherein the surface-active agent is selected from the group consisting of Tween 80, Tween 20, PEG, cetyl alcohol, PVP, PVA, lanolin alcohol, and sorbitan monooleate, and wherein the reducing agent is selected from the group consisting of cystein, N-acetyl-cysteine, thioglycerol, sodium sulfide, and glutathione, and wherein the reducing agent is present in combination with a chelating agent.

The formulation of the present invention also includes a formulation comprising an amino acid, a sugar or sugar alcohol, and a surface active-substance, and a further formulation wherein the sugar is sucrose and the amino acid is His, as well as a further formulation comprising an additive selected from the group consisting of Tween 20, Tween 80, and PEG, as well as a further formulation, comprising sucrose, His, PEG, and Ile.

The instant invention also includes a formulation comprising a surface active agent, wherein the agent is PEG, and a further formulation comprising a sugar and a reducing agent, and an additional formulation wherein the sugar is sucrose, and wherein the reducing agent is selected from the group consisting of cystein, N-acetyl cysteine, and thioglycerol, as well as an additional formulation further comprising an amino acid and a chelating agent.

The instant invention also comprehends a formulation, wherein the concentration of the transglutaminase is in the range from about 0.003 to about 50 mg/ml, and wherein the concentration of the amino acid, salt, derivative, and homolog thereof is in the range from about 0.01% to about 10% (w/v), and additionally, wherein the concentration of the amino acid, salt, derivative, and homolog thereof is in the range from about 0.1% to about 3% (w/v).

The present invention further includes a formulation, wherein the concentration of the sugar and sugar alcohol is between about 0.1% and about 20% (w/v), and additionally wherein the concentration of the sugar and sugar alcohol is between about 0.2% and about 10% (w/v).

The instant invention also includes a formulation, wherein the concentration of the surface-active agent is between about 0.00001% and about 5% (w/v), and wherein the concentration of the surface-active agent is between about 0.0002% and about 0.1% (w/v).

The present invention also comprehends a formulation, wherein the concentration of the reducing agent is between about 0.001% and about 2% (w/v), as well as a formulation, wherein the concentration of the reducing agent is between about 0.005% and about 0.5% (w/v).

The instant invention further includes a formulation, wherein the pH of the formulation is in a range from about 6 to about 9, or wherein the pH of the formulation is in a range from about 7 and about 8.

The formulation of the present invention also comprehends using a borate buffer and a chelating agent or a Tris buffer and a chelating agent.

The instant invention further includes a process for preparing a stable protein preparation comprising mixing a purified protein with a solution comprising at least one additive selected from the group consisting of: D- and L-amino acids and salts, derivatives, homologs, dimers, and oligomers thereof; sugars or sugar alcohols; surface-active agents; and reducing agents, with the proviso that the additive is neither glycine nor arginine. Additionally, the present invention comprehends freeze-drying the solution.

The present invention also comprehends that the protein used in the above preparation is a transglutaminase, and in particular that the protein is a Factor XIII.

The present invention also includes a pharmaceutical composition comprising a transglutaminase which has been stabilized according to the above process, as well as a pharmaceutical containing F XIII which has been stabilized according to above process.

The present invention also includes a method of treating a patient suffering from a disease characterized by a transglutaminase deficiency, comprising reconstituting the pharmaceutical composition according to the above process in an aqueous solution, and administering the resulting mixture to the patient, and furthermore wherein the mixture is administered topically or parenterally, and additionally, wherein the transglutaminase used is Factor XIII.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF PREFERRED EMBODIMENTS

The present invention provides stable preparations of transglutaminase by using defined stabilizers or mixtures thereof. The invention also provides processes for producing these stabilized preparations, and methods for their use.

The present invention relates to a stable preparation of a transglutaminase which, following lyophilization, is readily soluble without turbidity and which comprises a purified transglutaminase together with one or more stabilizers selected from the group consisting of: D- and L-amino acids other than glycine and arginine, their salts, derivatives and homologues, or dimers or oligomers thereof; sugars or sugar alcohols; surface-active agents; and reducing agents.

The embodiments described below demonstrate stable preparations of recombinant F XIII and of F XIII isolated from placenta or plasma, but the skilled artisan will recognize that the present invention is not limited to these embodiments, but may be applied to stable preparations of any transglutaminase presently known or that is discovered in the future. In a preferred embodiment, the present invention relates to stable preparation forms of factor XIII, and to preparations of biologically active fragments, derivatives or muteins thereof.

Such fragments, derivatives, and muteins include substitutional, insertional and deletional variants. Insertional variants comprise amino and/or carboxyl terminal fusions as well as intrasequence insertions of single or multiple amino acid residues. Insertions can be introduced within the mature coding sequence of the transglutaminase or factor XIII protein.

Deletion variants are characterized by the removal of one or more amino acid residues from the transglutaminase or factor XIII protein. These variants ordinarily are prepared by site specific mutagenesis of nucleotides in the DNA encoding the protein, thereby producing DNA encoding the variant, and thereafter expressing the DNA in recombinant cell culture. However, variant protein fragments may also be prepared by in vitro synthesis.

While the site for introducing an amino acid sequence variation ordinarily is predetermined, the mutation itself need not be predetermined. For example, in order to optimize the performance of a mutation at a given site, random mutagenesis may be conducted at the target codon or region and the expressed protein variants screened for the optimal combination of desired activity. Techniques for making substitution mutations at predetermined sites in DNA having a known sequence are well known, for example, M13 primer mutagenesis.

Substitutional variants are those where at least one residue sequence has been removed and a different residue inserted in its place. Amino acid substitutions are typically of single residues; insertions usually will be in order of about from 1 to 10 amino acid residues; and deletions will range from about 1 to 30 residues. Deletions or insertions preferably are made in adjacent pairs, i.e., a deletion of 2 residues or insertion of 2 residues. Substitutions, deletions, insertions or any combination thereof may be combined to arrive at a final construct. Obviously, the mutations that will be made in the DNA encoding the variant protein must not place the sequence out of reading frame and preferably will not create complementary regions that could produce secondary mRNA structure.

In a particularly preferred embodiment, the stable preparation forms comprise F XIII from plasma, placenta, thrombocytes or macrophages/monocytes, or comprise recombinant F XIII.

To develop the compositions of the present invention, various methods of freeze drying were studied, together with their effects on the subsequent stability of the compositions during storage. The factor XIII used in these studies was either rF XIII, prepared by the method of Metzner et al. (in McDonagh et al., "Factor XIII", 87–93, Schattauer (1993)) or placental or plasma F XIII, prepared as described by Karges et al. (in McDonagh et al., supra, at 66–76). Freeze-drying experiments were carried out in commercially available lyophilizers using small glass bottles with and without a siliconized surface.

Effects of Freeze-drying

To study the effects of freeze drying, purified recombinant or placental F XIII is mixed with solution of stabilizers, and the activity of the solution is determined in order to attain the given activities. Methods of measuring F XIII activity are well known in the art. F XIII activity may also be measured using commercially available kits, such as the Berichrom F XIII$^R$ test kit. The F XIII solutions are filtered and used to fill small glass bottles, which are then freeze dried. Methods of freeze drying are well known to those of skill in the art. Freeze drying can also be carried out in accordance with the instructions provided by the manufacturer of the lyophilized used.

After freeze drying, the lyophilisates are reconstituted to their original volume using distilled water. F XIII activities are determined as before and compared to the activity measured before freeze-drying. The reconstituted solutions are visually assessed with regard to turbidity. The results obtained using additives such as D- and/or L-amino acids, their salts, derivatives or homologues are described in Table I. Surprisingly, it was found that some of these additives preserved the activity and solubility of the F XIII very well during freeze-drying. In a preferred embodiment of the present invention, the stable transglutaminase composition comprises at least one of the amino acids D- or L- His, Glu, Met, Thr, Lys, Ala, Ile or Cys, or their physiologically acceptable salts, derivatives or homologs, dimers or oligomers thereof. Suitable derivatives and homologs are well known to one skilled in the art. Suitable derivatives include, but are not limited to: esters, thioesters, and amides of the carboxyl group; acylated derivatives of the amino group, including urethane derivatives; and esters, amides, and esters of side-chain functional groups. Suitable homologs include, for example, ornithine (homolog of lysine), homoserine, and α-aminobutyric acid. One skilled in the art would be able to use the methods described above to analyze the effects on stability of additives in a stable transglutaminase with only routine experimentation. Physiologically acceptable salts are also well known in the art and are described in, for example, REMINGTON'S PHARMACEUTICAL SCIENCES: DRUG RECEPTORS AND RECEPTOR THEORY, (18th ed.), Mack Publishing Co., Easton Pa. (1990). One skilled in the art would be able to use the methods described above to analyze the effects on stability of additives in a stable transglutaminase with only routine experimentation.

The amino acids His and Glu, especially, exhibited surprisingly good stabilization during freeze-drying, even in the absence of further additives. Conversely the amino acids Gly, Met or Ala, when used alone, produced a perceptible decline in activity during freeze-drying. See Table I.

The effect of sugars or sugar alcohols was also investigated. In some cases, the use of sugars or sugar alcohols on their own afforded good stabilization during the course of the freeze-drying (Table I). In particular, sugars or sugar alcohols such as sucrose, trehalose, lactose, maltose, sorbitol, mannitol, or the like, gave positive results. The decline in activity observed following freeze-drying when using amino acids that are not sufficiently effective on their own (such as Met or Ala) can be markedly reduced by combining the amino acids with sugars or sugar alcohols. See Table I. In a preferred embodiment of the present invention, therefore, stable preparation forms of a transglutaminase comprise at least one sugar or sugar alcohol selected from the group consisting of sucrose, lactose, trehalose, maltose, sorbitol or mannitol, their derivatives, homologs or mixtures thereof.

Only negligible stabilization was achieved when buffering substances such as Tris or phosphate were employed on their own. The use of borate buffers, however, surprisingly resulted in perceptible stabilization during freeze-drying. See Table I.

A slight protein precipitate may be observed occasionally when the lyophilisate is dissolved. This may be averted by using surface-active substances such as Tween 80 or Tween 20, polyethylene glycol (PEG) of molecular weights between 1000 and 35000 Da, cetyl alcohol, polyvinylpyrrolidone (PVP), polyvinyl alcohol (PVA), lanolin alcohol, or sorbitan monooleate, without loss of F XIII activity during freeze-drying. See Tables II and III. In a further preferred embodiment, the stable preparation forms comprise, therefore, a surface-active substance selected from the group consisting of Tween 80, Tween 20, PEG, cetyl alcohol, PVP, PVA, lanolin alcohol and sorbitan monooleate.

Stability during storage

A critical parameter of the formulated lyophilisate is its storage stability. This is determined both at 4° C. and at room temperature, and also under accelerated conditions at 37° C.

A combination of amino acids and sugars, sugar alcohols or sugar derivatives is particularly advantageous for good storage stability. See Table IV. Sugars such as sucrose, lactose, trehalose or maltose are found to stabilize activity even following relatively long storage periods at elevated temperature, whereas reducing sugars such as glucose or fructose appear unable to prevent a slow decline in activity at 37° C. See Table V. When the amino acids His or Glu, which give rise to good stability even on their own, are combined with sugars, still higher stability is produced. In a further preferred embodiment, therefore, the stable transglutaminase compositions comprise, as stabilizer, sucrose, maltose, trehalose, lactose, sorbitol or mannitol, or their derivatives or homologs, or mixtures thereof, in combination with the amino acid His, Glu, Ile and/or Ala.

As described supra, surface-active substances had no negative effects on storage stability when used in the appropriate concentration range. See Tables II and III.

Although F XIII does not possess any accessible SH groups, it is surprisingly found that thiol-containing agents such as Cys, N-acetylcysteine, thioglycerol or glutathione exhibit a positive effect on the storage stability of F XIII, especially at elevated temperatures. Chelating agents such as EDTA or citrate may be added to the composition to protect the thiol functions. In a further preferred embodiment, therefore, the novel, stable preparation form of a transglutaminase comprises Cys, N-acetyl-Cys, thiolglycerol, sodium sulfide or glutathione, or mixtures thereof, and may further comprise a chelating agent.

Very good results as regards maintaining the activity and the solubility of the lyophilisate are achieved using three or four component mixtures of amino acid(s), sugar and surface-active components, for example using mixtures of His/Tween/sucrose, His/PEG/sucrose, or His/Ile/PEG/sucrose. In a further preferred embodiment, therefore, the novel, stable preparation form of a transglutaminase comprises at least one additive selected from the group consisting of an amino acid, a sugar or sugar alcohol and surface-active substance, together with an additive mixture selected from the group consisting of His/Tween 20/sucrose, His/Tween 80/sucrose, His/PEG/sucrose or His/Ile/PEG/sucrose.

With respect to providing enhanced stability during storage, suitable formulation systems include mixtures composed of at least one amino acid, sugar, sugar alcohol, surface-active substance or reducing agent. For example, mixtures composed of amino acid(s)/Cys or N-acetyl-Cys/PEG/sucrose, amino acid(s)/thioglycerol/PEG/sucrose and sugar/reducing agent/PEG proved to be especially effective at maintaining stability at higher temperatures. See Tables III and VI. In a further preferred embodiment, therefore, the novel preparation form comprises a mixture composed of one or more of the group consisting of amino acids, sugars, sugar alcohols, surface-active substances, and reducing agents. Additional preferred embodiments include the mixtures amino acid(s)/Cys/PEG/sucrose, amino acid(s)/N-acetyl-Cys/PEG/sucrose, amino acid(s)/thioglycerol/PEG/sucrose and sugar/reducing agent/PEG, each optionally further comprising a chelating agent.

In the formulations described above, the concentration of F XIII employed can be varied in a wide range, and is preferably in the range of 0.003–50 mg/ml. The concentrations of the amino acids employed are preferably in a range of 0.01–10% (w/v), more preferably in the range of 0.1–3% (w/v). Sugar concentrations are preferably 0.1–20% (w/v), more preferably between 0.2 and 10% (w/v). Surface-active components may be employed in a preferred concentration range of 0.00001–5% (w/v), particularly preferably between 0.0002% and 0.1%. The concentrations of the reducing agents are preferably between 0.001% and 2% (w/v), particularly preferably between 0.005% and 0.5%.

The level of residual moisture is also important for the stability of the lyophilized protein during storage. Using the additives described above, the temperature of the composition can be raised to 50–60° C. for several hours, without any loss of activity, if this is necessary for reducing residual moisture during a final phase of the freeze-drying.

For freeze-drying transglutaminases and also for their subsequent stability during storage, the pH of the solutions should preferably be in the range of about 6 to about 9, particularly preferably between about 7 and about 8. The amino acids described above or phosphate buffers, borate buffers or Tris buffers having a pH in the range of about 6 to about 9, which are used, where appropriate, in combination with a chelating agent, are preferred for effecting the buffering.

The present invention also encompasses the use of the above-described stabilization additives for preparing stable liquid preparations comprising proteins other than transglutaminases, since the results obtained from the experiments described above are also applicable to other preparations. The present invention also encompasses a process for stabilizing proteins, preferably transglutaminases, in which at least one purified protein, which is preferably a transglutaminase, is mixed, as described above, as a solution or precipitate, with a solution containing one or more of the additives described above, is adjusted to a pH range which is advantageous for stability, and is then freeze-dried.

Because of the outstanding properties of the stabilized transglutaminases prepared in accordance with the methods described above, these transglutaminases are particularly suited for formulating pharmaceutical preparations of transglutaminases. The present invention also includes the use of stable preparation forms comprising Factor XIII, or biologically active fragments, derivatives or muteins thereof, for preparing a pharmaceutical for treating, for example, diseases which are characterized by F XIII deficiency. The novel pharmaceuticals can be formulated, in accordance with methods well known in the art, together with suitable pharmaceutically tolerated excipients. Methods for using F XIII are well known in the art of medicine. Dosages are also well known in the art and can readily be determined by a physician in attendance.

Stable transglutaminase preparations can be administered to patients following reconstitution with water, saline solutions or other suitable solvents. Any application route (e.g. intravenous, intradermal, subcutaneous, intramuscular, intraperitoneal, mucosal, topical etc.) may be used. The administered dose depend upon the disease being treated. For example, intravenous doses can be used to increase the systemic or local F XIII level significantly over the previous level. For substitution, only limited increases of F XIII may be necessary. During therapeutic application, it may be necessary to increase the F XIII plasma levels by several units of F XIII per ml by applying several thousands of units per dose.

The stable F XIII preparations of the invention are useful in systemic or local application to treat conditions including bone or would healing, ulcerative colitis, schleroderma, Sch ölein Henoch purpura, subarchnoidal hemorrhage, intraventricular bleeding, bleedings during surgery, and bleedings for unknown reasons.

The present invention, thus generally described, will be understood more readily by reference to the following examples, which are provided by way of illustration and are not intended to be limiting of the present invention.

EXAMPLE 1

Freeze Drying of Factor XIII rF XIII, prepared by expression in yeast cells and purified to a purity of >98%, and placental F XIII, also in purified form, were treated, as a solution or as a precipitate, with solutions of the stabilizers in order to attain the given activities. The F XIII solutions were filtered, used to fill small glass bottles and dried in accordance with a suitable freeze-drying program. The lyophilisates were then reconstituted once again to their original volume using distilled water. F XIII activities were determined before and after freeze-drying. In addition, the reconstituted solution was assessed with regard to turbidity. The activity of the F XIII was determined using the commercially available Berichrom F XIII$^R$ test kit.

The results presented in Tables I, II and III demonstrate unambiguously that it is necessary to add the novel stabilizing constituents when freeze-drying F XIII and that the enzymatic activity and the solubility can be preserved by adding amino acids or sugars or amino acids and sugars even without the additional use of HSA. The solubility, in particular, can in some cases be still further improved by adding surface-active agents.

EXAMPLE 2

Stability of F XIII Preparations

Lyophilisates of rF XIII and placental F XIII, prepared as indicated in Example 1, were stored at 4° C. or at 37° C. for various times and were then reconstituted with AQUA INJECTAB™ or with sodium chloride solution. The enzyme activity which remained was then measured.

The results presented in Tables II and VI demonstrate that long-term stabilization can be achieved using the mixtures described above comprising an amino acid or amino acids and/or sugars or sugar derivatives. The addition of a reducing component leads in some cases to a further increase in stability, particularly under accelerated conditions.

TABLE I

Freeze-drying FXIII

| | Activity before lyophi-lis. % | Activity of the lyophilisate (in % of the starting value) | Turbidity after dissolving the lyophilisate |
|---|---|---|---|
| — | 100 | 2 | +++ |
| 10 mM Tris* HCl, pH 7.4 | 100 | 8 | + |
| 10 mM Na borate pH 8.0 | 100 | 68 | (–) |
| 1% L-His, phys. NaCl, pH 7.4 | 100 | 39 | ++ |
| 1% L-His, pH 7.6 | 100 | 100 | – |
| 1% L-Arg, pH 7.6 | 100 | 96 | +/– |
| 1% L-Gly, pH 7.6 | 100 | 41 | +/– |
| 1% L-Ala, pH 7.6 | 100 | 67 | +/– |
| 1% L-Glu, pH 7.6 | 100 | 88 | + |
| 1% L-Met, pH 7.6 | 100 | 10 | +++ |
| 1% L-His, 0.1% L-Ile, pH 7.6 | 100 | 99 | – |
| 1% sucrose | 100 | 92 | (–) |
| 2.5% sucrose | 100 | 91 | (–) |
| 5% sucrose | 100 | 83 | (–) |
| 2.5% lactose | 100 | 100 | (–) |
| 2.5% sorbitol | 100 | 92 | (–) |
| 2.5% trehalose | 100 | 99 | (–) |
| 2.5% maltose | 100 | 100 | (–) |
| 1% L-His, 2.5% sucr., pH 7.6 | 100 | 96 | (–) |
| 1% L-Arg, 2.5% sucr., pH 7.6 | 100 | 90 | + |
| 1% L-Ala, 2.5% sucr., pH 7.6 | 100 | 100 | – |
| 1% L-Glu, 2.5% sucr., pH 7.6 | 100 | 87 | + |
| 1% L-Lys, 2.5% sucr., pH 7.6 | 100 | 92 | (–) |
| 1% L-Met, 2.5% sucr., pH 7.6 | 100 | 91 | (–) |

TABLE I-continued

Freeze-drying FXIII

| | Activity before lyophi-lis. % | Activity of the lyophilisate (in % of the starting value) | Turbidity after dissolving the lyophilisate |
|---|---|---|---|
| 1% L-Thr, 2.5% sucr., pH 7.6 | 100 | 94 | +/– |
| 1% L-His, 0.1% L-Ile, 2.5% sucr., pH 7.6 | 100 | 94 | (–) |
| 1% L-His, 0.1% L-Ile, 2.5% gluc., pH 7.6 | 100 | 85 | – |
| 1% L-His, 0.1% L-Ile, 2.5% lact., pH 7.6 | 100 | 99 | (–) |
| 1% L-His, 0.1% L-Ile, 2.5% fruct., pH 7.6 | 100 | 92 | – |
| 1% L-His, 0.1% L-Ile, 2.5% sorbitol, pH 7.6 | 100 | 91 | (–) |
| 0.5% L-His, 0.1% L-Ile, 2.5% sucr., pH 7.6 | 100 | 95 | (–) |
| 1% L-His, 0.1% L-Ile, 1% sucr., pH 7.6 | 100 | 93 | (–) |
| 1% L-His, 0.1% L-Cys, 2.5% sucr., pH 7.6 | 100 | 107 | – |

Activity test: Berichrom FXIII
Turbidity:
– no turbidity
(–) minimal turbidity
+/– very low turbidity
+ slight, but very distinct, turbidity
++ marked turbidity
+++ very marked turbidity

TABLE II

Effect of surface-active substances on the solubility or stability of an FXIII lyophilisate

| | Activity before ly ophilization (U/ml) | Turbidity after dissolving | Activity (U/ml) at t = 0 | 0.5 | 1 | 2 | 3 | 6 | 12 | 24 mon. |
|---|---|---|---|---|---|---|---|---|---|---|
| 1% L-His, 0.1% L-lle, 2.5% sucr., pH 7.2 | 153 | + | 150 | 144 | 139 | | 139 | 143 | 136 | |
| 1% L-His, 0.1% L-lle, 2.5% sucr., pH 7.6 | 154 | + | 141 | 151 | 132 | | 132 | 139 | 136 | |
| 1% L-His, 0.1% L-lle, 2.5% sucr., pH 8.0 | 152 | + | 148 | 143 | 141 | | 141 | 138 | 137 | |
| 1% L-His, 0.1% L-lle, 2.5% sucr. | 129 | + | 124 | | 122 | 113 | 115 | 111 | 115 | 122 |
| 1% L-His, 2.5% sucr. | 131 | (–) | 125 | | 126 | 114 | 117 | 108 | 118 | 120 |
| 1% L-His, 0.01% PEG 4000, 2.5% sucr. | 128 | – | 119 | | 124 | 114 | 111 | 111 | 114 | 119 |
| 1% L-His, 0.001% PEG 4000, 2.5% sucr. | 130 | – | 123 | | 125 | 112 | 114 | 112 | 114 | 119 |
| 1% L-His, 0.0001% PEG 4000, 2.5% sucr. | 130 | – | 118 | | 120 | 107 | 114 | 107 | 107 | 116 |
| 1% L-His, 0.001% Tween 20, 2.5% sucr. | 128 | – | 123 | | 124 | 112 | 114 | 113 | 119 | 119 |
| 1% L-His, 0.0001% Tween 20, 2.5% sucr. | 130 | – | 122 | | 124 | 112 | 111 | 105 | 112 | 120 |
| 1% L-His, 10 mM citrate, 2.5% sucr. | 156 | (–) | 149 | 146 | 138 | | 143 | 136 | 147 | |
| 1% L-His, 0.01% PEG 4000, 2.5% sucr. | 155 | – | 147 | 138 | 137 | | 140 | 134 | 135 | |
| 1% L-His, 0.1% L-Cys, 2.5% sucr. | 156 | – | 156 | 156 | 146 | | 148 | 153 | 151 | |

Storage of the samples at +4° C.
pH 7.6, unless otherwise indicated
Activity test: Berichrom FXIII (U/ml)
Turbidity: - no turbidity
(–) minimal turbidity
+ slight, but very distinct, turbidity

TABLE III

| | Storage of FXIII lyophilisate<br>Storage of the samples at room temperature | | | | | | |
|---|---|---|---|---|---|---|---|
| | Activity | Activity (U/ml) at t = | | | | | |
| | before storage (U/ml) | 1 mon. (U/ml) | 3 mon. (U/ml) | 6 mon. (U/ml) | 9 mon. (U/ml) | 12 mon. (U/ml) | Turbidity after t = 1 mon. |
| 1% His/0.001% PEG 4000/2.5% sucr./pH 7.6 | 85 | 99 | 89 | 84 | 86 | 69 | (–) |
| 1% His/0.1% cysteine/0.001% PEG 4000/2.5% sucr./pH 7.6 | 92 | 110 | 97 | 103 | 110 | 91 | – |
| 1% His/0.01% cysteine/0.001% PEG 4000/2.5% sucr./pH 7.6 | 87 | 108 | 96 | 98 | 104 | 85 | – |
| 1% His/0.005% PEG 4000/2.5% sucr./pH 7.6 | 99 | 109 | 103 | 99 | 94 | 79 | – |
| 1% His/0.01% PVP 15/2.5% sucr./pH 7.6 | 94 | 105 | 96 | 96 | 88 | 78 | – |
| 1% His/0.1% lle/0.001-% PEG 4000/2.5% sucr./pH 7.6 | 101 | 106 | 92 | 84 | 90 | 69 | – |

Activity test: Berichrom FXIII
Turbidity: - no turbidity
(–) minimal turbidity

TABLE IV

| | Storage of rhuXIII lyophilisate at 4° C. | | | | | | | | |
|---|---|---|---|---|---|---|---|---|---|
| | Activity before | Activity (U/ml) of the lyophilisate at t = | | | | | | | |
| | lyophillsation (U/ml) | 0 | 0.5 mon | 1 mon | 3 mon | 6 mon | 12 mon | 18 mon | 24 mon |
| 1% L-His pH 7.8 | 125 | 150 | 112 | 95 | 111 | 82 | 100 | 108 | 100 |
| 1% L-Gly pH 7.6 | 125 | 61 | 26 | 48 | 34 | 30 | 29 | 25 | 16 |
| 1% L-Glu pH 7.6 | 125 | 132 | 127 | 116 | 110 | 77 | 114 | 83 | 93 |
| 1% L-His, 2.5% sucr., pH 7.6 | 125 | 144 | 112 | 106 | 133 | 97 | 111 | 109 | 94 |
| 1% L-Arg, 2.5% sucr., pH 7.6 | 125 | 134 | 113 | 106 | 118 | 88 | 113 | 60 | 89 |
| 1% L-Ala, 2.5% sucr., pH 7.6 | 125 | 150 | 124 | 98 | 114 | 71 | 127 | 102 | 118 |
| 1% L-Glu, 2.5% sucr., pH 7.6 | 125 | 130 | 108 | 110 | 122 | 84 | 140 | 104 | 90 |
| 1% sucrose | 160 | 153 | 130 | 139 | 136 | 137 | 141 | 129 | 146 |
| 2.5% sucrose | 160 | 148 | 127 | 135 | 128 | 135 | 130 | 126 | 141 |
| 5% sucrose | 160 | 130 | 109 | 117 | 113 | 109 | 114 | 107 | 121 |
| 2.5% lactose | 160 | 163 | 136 | 146 | 137 | 137 | 137 | 131 | 158 |
| 2.5% sorbitol | 100 | 146 | 122 | 132 | 125 | 122 | 123 | 124 | 148 |
| 2.5% trehal-ose | 160 | 160 | 136 | 142 | 137 | 141 | 136 | 127 | 138 |
| 2.5% maltose | 160 | 155 | 134 | 139 | 132 | 118 | 139 | 123 | 150 |
| 1% L-His, 0.1% L-lle, pH 7.6 | 125 | 148 | 136 | 126 | 93 | 100 | 116 | 105 | 102 |
| 0.5% L-His, 0.1% L-lle, 2.5% sucr., pH 7.6 | 125 | 142 | 123 | 113 | 119 | 93 | 116 | 106 | 100 |
| 1% L-His, 0.1% L-lle, 1% sucr., pH 7.6 | 125 | 139 | 112 | 109 | 127 | 94 | 87 | 108 | 103 |

TABLE IV-continued

| Storage of rhuXIII lyophilisate at 4° C. | | | | | | | | | |
|---|---|---|---|---|---|---|---|---|---|
| | Activity before lyophillsation (U/ml) | Activity (U/ml) of the lyophilisate at t = | | | | | | | |
| | | 0 | 0.5 mon | 1 mon | 3 mon | 6 mon | 12 mon | 18 mon | 24 mon |
| 1% L-His, 0.1% L-Cys, 2.5% sucr., pH 7.6 | 125 | 161 | 135 | 120 | 113 | 91 | 112 | 112 | 101 |

Activity test: Berichrom FXIII

TABLE V

| Storage of FXIII lyophilisate at 37° C. | | | | | | |
|---|---|---|---|---|---|---|
| | Activity before lyophil. (U/ml) | Activity (U/ml) of the lyophilisate at t = | | | | |
| | | 0 | 1 mon | 3 mon | 6 mon | 12 mon |
| 1% L-His, 0.1% L-lle, 2.5% sucr., pH 7.6 | 444 | 394 | 405 | 311 | 300 | 212 |
| 1% L-His, 0.1% L-lle, 2.5% glucose pH 7.6 | 440 | 373 | 358 | 152 | 34 | 3 |
| 1% L-His, 0.1% L-lle, 2.5% lactose pH 7.6 | 424 | 419 | 385 | 322 | 293 | 285 |
| 1% L-His, 0.1% L-lle, 2.5% fructose, pH 7.6 | 423 | 387 | 385 | 37 | 11 | 3 |
| 1% L-His, 0.1% L-lle, 2.5% sorbitol pH 7.6 | 420 | 380 | 298 | 120 | 64 | 21 |
| 1% L-His, 0.1% L-lle, 2.5% maltose pH 7.6 | 425 | 366 | 393 | 316 | 293 | 293 |
| 1% L-His, 0.1% L-lle, 0.1% L-Cys, 2.5% sucrose, pH 7.6 | 413 | 408 | 418 | 350 | 354 | 393 |
| 1% L-Glu, 0.1% L-lle, 2.5% sucr., pH 7.6 | 424 | 395 | 350 | 281 | 301 | 314 |
| 1% L-Lys, 0.1% L-lle, 2.5% sucr., pH 7.6 | 423 | 350 | 403 | 328 | 318 | 333 |

Activity test: Berichrom FXIII

TABLE VI

| | Activity before lyophil. (U/ml) | Activity (U/ml) after various storage times at +4° C. in months | | | | | | |
|---|---|---|---|---|---|---|---|---|
| | | 0 | 0.5 mon | 1 mon | 3 mon | 7 mon | 12 mon | 24 mon |
| Storage of FXIII lyophilisate at various temperatures | | | | | | | | |
| 1% His/0.001% PEG/2.5% cysteine/ sucr./0.2% pH 7.6 | 112 | 118 | 119 | 117 | 116 | 115 | 122 | 120 |

TABLE VI-continued

| | | | | | | | | |
|---|---|---|---|---|---|---|---|---|
| 1% His/0.001% PEG/2.5% sucr./ 0.2% N-acetyl-cysteine/pH 7.6 | 112 | 113 | 123 | 120 | 125 | 118 | 120 | 125 |
| 1% His/0.001% PEG/2.5% sucr./ 0.2% thioglycerol/ pH 7.6 | 119 | 109 | 125 | 122 | 129 | 116 | 129 | 131 |
| 1% His/0.001% PEG/2.5% sucr./ pH 7.6 | 119 | 109 | 117 | 110 | 118 | 109 | 113 | 116 |
| | | 0 | 0.5 mon | 1 mon | 3 mon | 7 mon | 12 mon | 24 mon |
| | | Storage at room temperature | | | | | | |
| 1% His/0.001% PEG/2.5% sucr./0.2% cysteine/pH 7.6 | 112 | 118 | 119 | 115 | 116 | 114 | 120 | 112 |
| 1% His/0.001% PEG/2.5% sucr./0.2% N-acetylcysteine/pH 7.6 | 112 | 113 | 112 | 114 | 120 | 122 | 122 | 120 |
| 1% His/0.001% PEG/2.5% sucr./0.2% thioglycerol/pH 7.6 | 119 | 109 | 123 | 121 | 120 | 116 | 118 | 116 |
| 1% His/0.001% PEG/2.5% sucr./pH 7.6 | 119 | 109 | 117 | 108 | 109 | 105 | 100 | 98 |
| | | 0 | 0.5 mon | 1 mon | 3 mon | 7 mon | 12 mon | 24 mon |
| | | Storage at +37° C. | | | | | | |
| 1% His/0.001% PEG/2.5% sucr./0.2% cysteine/pH 7.6 | 112 | 118 | 121 | 114 | 119 | 119 | 104 | 89 |
| 1% His/0.001% PEG/ 2.5% sucr./0.2% N-acerylcysteine/pH 7.6 | 112 | 113 | 119 | 111 | 112 | 102 | 107 | 89 |
| 1% His/0.001% PEG/2.5% sucr./0.2% thioglycerol/pH 7.6 | 119 | 109 | 119 | 120 | 113 | 95 | 98 | 85 |
| 1% His/0.001% PEG/2.5% sucr./pH 7.6 | 119 | 109 | 107 | 108 | 100 | 85 | 78 | 57 |

Activity test: Berichrom FXIII

What is claimed is:

1. A stable lyophilized transglutaminase formulation, comprising at least one additive selected from the group consisting of: D- and L- amino acids and salts, derivatives, homologs and dimers thereof, sugars or sugar alcohols; surface active agents; and reducing agents, with the proviso that said additive is neither glycine nor arginine, wherein said formulation does not contain a protein stabilizer and wherein said formulation is soluble without any turbidity in an aqueous solvent suitable for parenteral administration to a human patient.

2. The formulation according to claim 1, wherein said transglutaminase is selected from the group consisting of Factor XIII, and biologically active fragments, derivatives, and muteins thereof.

3. The formulation according to claim 2, wherein said Factor XIII is recombinant Factor XIII or is isolated from plasma, placenta, thrombocyte, or macrophages/monocytes.

4. The formulation according to claim 2, wherein said amino acid is selected from the group consisitn of His, Glu, Met, Thr, Lys, Ala, Ile, or Cys, and the salts, derivatives, homologs, dimers and oligomers thereof.

5. The formulation according to claim 1, wherein said sugar or sugar alcohol is selected from the group consisting of sucrose, maltose, trehalose, lactose, sorbitol, mannitol, and the derivatives, and homologs thereof.

6. The formulation according to claim 5, further comprising an amino acid selected from the group consisting of His, Glu, Ile and Ala.

7. The formulation according to claim 1, wherein said surface-active agent is selected from the group consisting of Tween 80, Tween 20, PEG, cetyl alcohol, PVP, PVA, lanolin alcohol, and sorbitan monooleate.

8. The formulation according to claim 1, wherein said reducing agent is selected from the group consisting of cysteine, N-acetyl-cysteine, thioglycerol, sodium sulfide, and glutathione, and wherein said reducing agent is present in combination with a chelating agent.

9. The formulation according to claim 1, comprising an amino acid, a sugar or sugar alcohol, and a surface active-substance.

10. The formulation according to claim 9, wherein said sugar is sucrose and said amino acid is His.

11. The formulation according to claim 10, further comprising an additive selected from the group consisting of Tween 20, Tween 80, and PEG.

12. The formulation according to claim 11, comprising sucrose, His, PEG, and Ile.

13. The formulation according to claim 1, comprising a surface active agent, wherein said agent is PEG.

14. The formulation according to claim 13, further comprising a sugar and a reducing agent.

15. The formulation according to claim 14, wherein said sugar is sucrose, and wherein said reducing agent is selected from the group consisting of cystein, N-acetyl cysteine, and thioglycerol.

16. The formulation according to claim 15, further comprising an amino acid.

17. The formulation according to claim 16, further comprising a chelating agent.

18. The formulation according to claim 1, wherein the concentration of said transglutaminase is in the range from about 0.003 to about 50 mg/ml.

19. The formulation according to claim 1, wherein the concentration of said amino acid, salt, derivative, and homolog thereof is in the range from about 0.01% to about 10% (w/v).

20. The formulation according to claim 19, wherein the concentration of said amino acid, salt, derivative, and homolog thereof is in the range from about 0.1% to about 3% (w/v).

21. The formulation according to claim 1, wherein the concentration of said sugar and sugar alcohol is between about 0.1% and about 20% (w/v).

22. The formulation according to claim 21, wherein the concentration of said sugar and sugar alcohol is between about 0.2% and about 10% (w/v).

23. The formulation according to claim 1, wherein the concentration of said surface-active agent is between about 0.00001% and about 5% (w/v).

24. The formulation according to claim 23, wherein the concentration of said surface-active agent is between about 0.0002% and about 2% (w/v).

25. The formulation according to claim 1, wherein the concentration of said reducing agent is between about 0.001% and about 2% (w/v).

26. The formulation according to claim 25, wherein the concentration of said reducing agent is between about 0.005% and about 0.5% (w/v).

27. The formulation according to claim 1, wherein the pH of said formulation is in a range from about 6 to about 9.

28. The formulation according to claim 27, wherein the pH of said formulation is in a range from about 7 and about 8.

29. The formulation according to claim 27, further comprising a borate buffer and a chelating agent.

30. The formulation according to claim 27, further comprising a Tris buffer and a chelating agent.

31. A process for preparing a stable protein transglutaminase comprising mixing a purified transglutaminase with an aqueous solution suitable for parenteral administration to a human patient and lyophilizing the resultant mixture wherein said solution comprises at least one additive selected from the group consisting of: D- and L- amino acids and salts, derivatives, homologs and dimers thereof, sugars or sugar alcohols; surface active agents; and reducing agents, with the proviso that said additive is neither glycine nor arginine, wherein said formulation does not contain a protein stabilizer, and wherein said purified transglutaminase dissolves in said aqueous solution without any turbidity.

32. The process according to claim 31, wherein said protein is Factor XIII.

33. A pharmaceutical composition comprising a transglutaminase formulation according to claim 1.

34. A pharmaceutical composition comprising a F XIII formulation according to claim 2.

35. A method of treating a patient suffering from a disease characterized by a transglutaminase deficiency, comprising reconstituting the pharmaceutical composition according to claim 23 in an aqueous solution, and administering the resulting mixture to the patient.

36. The method according to claim 35, wherein said mixture is administered topically or parenterally.

37. The method according to claim 36, wherein said transglutaminase is Factor XIII.

* * * * *